United States Patent [19]
Debregeas et al.

[11] Patent Number: 6,139,877
[45] Date of Patent: Oct. 31, 2000

[54] SPHEROIDS CONTAINING TIAGABINE, PREPARATION PROCESS AND PHARMACEUTICAL COMPOSITIONS

[75] Inventors: Patrice Debregeas, Paris; Gérard Leduc, Malesherbes; Pascal Oury, Paris; Pascal Suplie, Montaure, all of France

[73] Assignee: Laboratoires des Produits Ethiques Ethypharm, Houdan, France

[21] Appl. No.: 09/198,564

[22] Filed: Nov. 23, 1998

[30] Foreign Application Priority Data

Nov. 21, 1997 [FR] France ................. 979 14635

[51] Int. Cl.⁷ ............... A61K 9/16; A61K 9/20; A61K 9/26; A61K 9/48; A61K 31/445
[52] U.S. Cl. ............ 424/490; 424/461; 424/462; 424/469; 424/494; 424/497; 514/326
[58] Field of Search ............... 424/451, 461, 424/462, 464, 469, 489, 490, 494, 497; 514/326, 960, 963, 965

[56] References Cited

U.S. PATENT DOCUMENTS

| | | | |
|---|---|---|---|
| 5,326,570 | 7/1994 | Rudnic et al. | 424/458 |
| 5,430,021 | 7/1995 | Rudnic et al. | 514/14 |
| 5,447,729 | 9/1995 | Belenduik et al. | 424/490 |
| 5,484,608 | 1/1996 | Rudnic et al. | 424/468 |
| 5,591,451 | 1/1997 | Gupta et al. | 424/464 |
| 5,750,140 | 5/1998 | Weibel et al. | 424/449 |
| 5,863,558 | 1/1999 | Jao et al. | 424/465 |
| 5,866,590 | 2/1999 | Svensson et al. | 514/326 |
| 5,876,750 | 3/1999 | Jao et al. | 424/457 |
| 5,906,832 | 5/1999 | Jao et al. | 424/465 |
| 5,912,013 | 6/1999 | Rudnic et al. | 424/465 |
| 5,914,333 | 6/1999 | Fink-Jensen | 514/326 |
| 5,955,103 | 9/1999 | Jao et al. | 424/457 |
| 6,008,192 | 12/1999 | Al-Razzak et al. | 514/11 |

FOREIGN PATENT DOCUMENTS

| | | |
|---|---|---|
| 0 361 874 | 4/1990 | European Pat. Off. . |
| 0 468 436 | 1/1992 | European Pat. Off. . |
| 92/17473 | 10/1992 | WIPO . |
| 95/05808 | 3/1994 | WIPO . |
| 95/31976 | 11/1995 | WIPO . |
| 96/34606 | 11/1996 | WIPO . |

*Primary Examiner*—Robert H. Harrison
*Attorney, Agent, or Firm*—Foley & Lardner

[57] ABSTRACT

The present invention relates to a novel pharmaceutical form, in the form of spheroids, containing tiagabine as active principle. The invention also covers the process for the preparation of such spheroids and multiparticulate pharmaceutical preparations, such as tablets, containing these spheroids. These pharmaceutical preparations are intended for the delivery of the spheroids they contain, and are characterized by the absence of an adverse effect on the release profile of the tiagabine contained in the spheroids following a possible compression step.

19 Claims, 1 Drawing Sheet

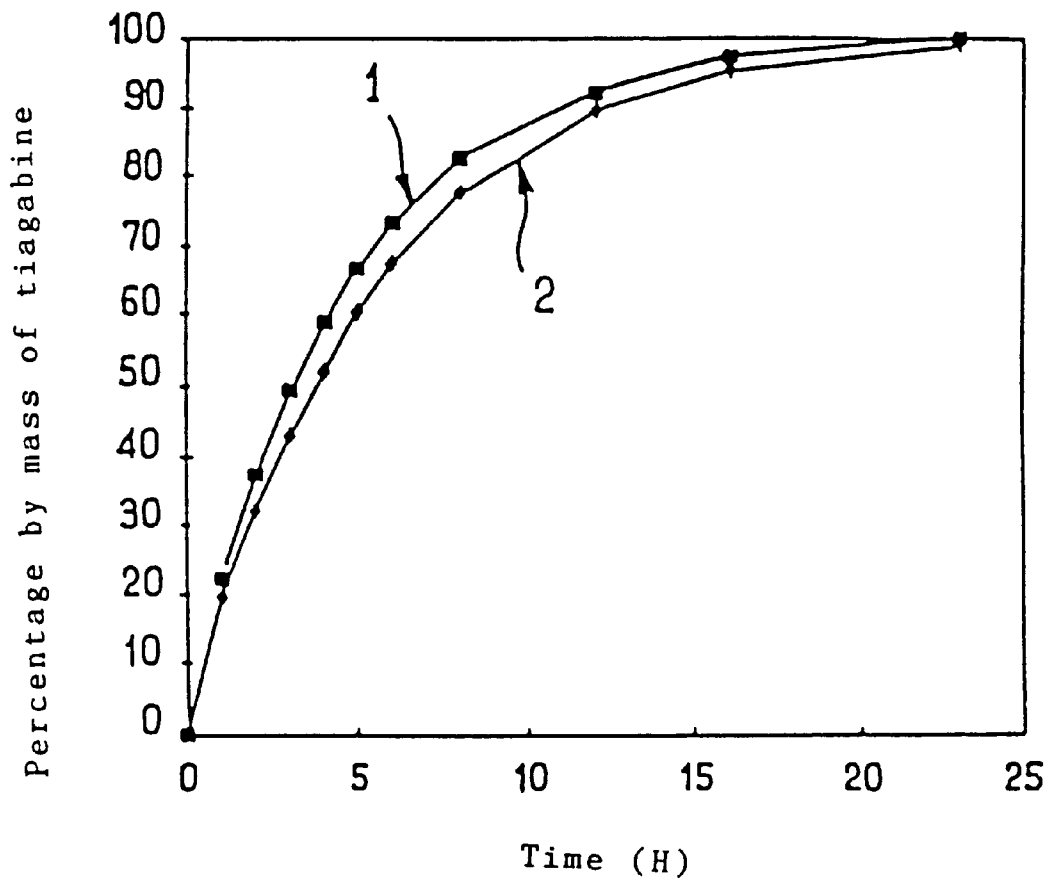
SINGLE FIGURE

SPHEROIDS CONTAINING TIAGABINE, PREPARATION PROCESS AND PHARMACEUTICAL COMPOSITIONS

The present invention relates to a novel pharmaceutical form, in the form of spheroids, containing tiagabine as active principle.

The invention also covers the process for the preparation of such spheroids and multiparticulate pharmaceutical preparations containing these spheroids. These pharmaceutical preparations are intended for the delivery of the spheroids they contain, and are characterized in that they do not adversely affect the release profile of the tiagabine contained in the spheroids.

The term spheroids is understood to refer to spherical units whose size can range from 0.25 mm to 3 mm, preferably from 0.5 mm to 1 mm.

U.S. Pat. No. 4,684,516 describes tablets for oral administration which disintegrate rapidly in aqueous medium, comprising coated granules capable of releasing an active principle at a controlled rate over several hours into the intestinal system and comprising 2 to 15% by weight of binders and lubricants.

U.S. Pat. No. 4,684,516 describes in particular granules obtained by application of a layer of active principle to unsimilar materials, these granules then being coated with a first film containing a mixture of stearic acid, carnauba wax and talc, and a second film consisting of disintegrating agents—such as starch, cellulose or alginic acid—which also serve to provide the tablet's cohesion.

Patent application EP 468,436 describes prolonged-release tablets obtained by compression of an active principle and of a mixture of two powders, one being hydrophobic and the other water-soluble. The hydrophobic powder is obtained by melting and spraying a mixture of stearic acid, glycerol and hydrogenated castor oil. The water-soluble powder is a cellulose mixed with lactose.

Patent application EP 548,356 describes multiparticulate tablets which are rapidly broken down, comprising an active substance in the form of monocrystals or microgranules.

These tablets are obtained by pregranulation of a mixture of excipients consisting of one or more breakdown agents of the carboxymethylcellulose or polyvinyl-pyrrolidone type, one or more swelling agents of the starch type and a direct compression sugar such as dextrose. The microgranules or monocrystals are dry-mixed into the mixture of excipients before being tabletted.

It has been shown that the excipients usually used to coat non-tabletted granules, such as cellulose derivatives, could not absorb the mechanical stresses to which the granules are subjected during compression (International Journal of Pharmaceutics, No. 143, 13–23, 1996).

The compression of coated granules is a delicate operation since it changes the structure of the coating film by causing fissures to appear or by rupture, which leads to the partial or total loss of the properties of the film.

Fissuration of the granules irreversibly changes the release profile of the active principle they contain.

In order to conserve the characteristics of the film coating the granules, before and after compression, the granules of the prior art are diluted with auxiliary substances whose role is to absorb the physical stresses associated with compression (binders) and to allow disintegration of the tablet (disintegrating agents) in liquid medium, i.e. in aqueous solution or in the digestive juices.

The tablet formulations of the prior art use auxiliary substances added to the granules during compression in order to avoid surface fissuration of these granules.

The subject of the present invention relates to spheroids containing tiagabine as active principle, which can be directly compressed without the addition of a substantial amount of an auxiliary substance, i.e. less than 5% by weight, preferably less than 1% by weight.

The subject of the present invention is spheroids containing tiagabine as active principle and comprising:

a core and/or a layer coating the said core, containing at least one thermoplastic excipient which is of pasty to semi-solid consistency at a temperature of about 20° C., and whose melting point is between about 25° C. and about 100° C., coated with a flexible and deformable film, based on a polymer material, in particular a film whose glass transition temperature is less than about 30° C., which ensures either protection or masking of the taste, or modified and controlled release of the tiagabine.

The core can be composed in particular of a mixture of sucrose and starch or microcrystalline cellulose.

In the context of the present invention, thermoplastic excipients is understood to refer to compounds having a melting point of between 25 and 100° C. and characterized by a pasty to semi-solid consistency at a temperature of the order of 20° C.

The role of the thermoplastic excipient is, in particular, during a possible compression step, to allow the spheroids to deform plastically, and thus to absorb some of the stresses to which they are subjected, such that their surface is not fissured or torn.

The thermoplastic excipient can advantageously be chosen from partially hydrogenated oils, beeswax, carnauba wax, paraffin waxes, silicone waxes, C12–C18 fatty alcohols and fatty acids, solid, semi-synthetic glycerides, glycerol monoesters, diesters or triesters, polyoxyethylene glycols, glycosylated polyoxyethylenated glycerides, and one of the mixtures thereof.

The layer containing at least one thermoplastic excipient is coated with a flexible and deformable film, comprising a polymer material, whose glass transition temperature is less than about 30° C., preferably less than about 20° C.

The polymer film comprises a polymer material which is either a polymer or a mixture of at least one polymer and a plasticizer.

The polymer film can serve, depending on the case, to protect the tiagabine from the environment (degradation by light, by ambient moisture), to mask the taste of the active principle or to modify its release (prolonged, delayed or programmed release).

The polymer is preferably an acrylic, vinyl or cellulose polymer or copolymer.

The term plasticizer is understood to refer to a product which lowers the glass transition temperature of the polymer.

The plasticizer is preferably chosen from triethyl citrate, acetyl triethyl citrate, tributyl citrate, acetyl tributyl citrate, triacetin, diethyl phthalate, polyethylene glycols, polysorbates, mono- and diacetylated glycerides, and mixtures thereof.

The mechanical properties of the polymer film, in particular the percentage of elongation and the breaking strength, can serve as selection criteria for the polymer and/or the plasticizer. These mechanical properties can also be determined by the method described in standards DIN53 455 and ISO/RI 184.

In the context of the present invention, a polymer or a polymer/plasticizer mixture having a percentage of elongation of greater than about 50% is preferably chosen, in order to coat spheroids intended to be compressed.

For example, the polymer Eudragit NE30D® sold by the company Röhm, which is a neutral copolymer of acrylic and methacrylic acid esters in the form of an aqueous 30% dispersion, has a percentage of elongation of 600% and a breaking strength equal to 8 N/mm², which makes it particularly flexible and deformable.

According to a first variant of the invention, the tiagabine is dispersed in the bulk of the core.

According to a second variant, the tiagabine is dispersed in the layer containing at least one thermoplastic excipient.

According to a third variant, the active principle is applied to the surface of the core and then coated with a layer containing at least one thermoplastic excipient.

Lastly, according to a fourth and final variant, the tiagabine is dispersed in the bulk of the core and in the layer containing at least one thermoplastic excipient.

The active principle can be protected, in one of the above four variants, by combining it with an antioxidant and/or by coating it with a protective film.

The spheroids according to the invention can advantageously be coated with a water-dispersible outer layer.

The outer layer provides the said spheroids with cohesion during a possible compression step, and ensures that the tablet obtained breaks down in aqueous medium.

The water-dispersible outer layer preferably consists of an acrylic, vinyl or cellulose polymer.

The subject of the present invention is also the process for the preparation of the spheroids described above.

The cores can be manufactured by assembly in a turbomixer from calibrated sucrose crystals, or by extrusion-spheronization.

When the cores are prepared by extrusion-spheronization, the tiagabine can be mixed into the extruded-spheronized bulk.

According to the preparation process of the invention, the layer containing at least one thermoplastic excipient, the film containing a polymer material, and optionally the outer protective layer, are successively deposited on the cores by spraying, in a granulating turbomixer, in a perforated turbomixer, in a fluidized-air bed, or by any other appropriate means.

The process according to the invention comprises two or three steps depending on whether it is desired to prepare spheroids containing an outer layer which is water-dispersible, or otherwise.

The spheroids containing a water-dispersible outer layer are particularly suitable for the preparation of tablets.

The first step, known as the assembly step, consists in depositing the thermoplastic excipient(s) onto the cores. The assembly preparation can, depending on the case, be in the form of solid dispersions in aqueous or organic media, in the form of solutions, in the form of emulsions or in the molten state.

When the tiagabine is dispersed in the bulk of the layer containing at least one thermoplastic excipient, the active principle is incorporated into the assembly preparation.

According to another variant of the process according to the invention, the active principle can be bound by dusting onto the neutral cores premoistened with the assembly preparation.

According to other embodiments, the tiagabine can be dispersed in the bulk of the core or both in the bulk of the core and in that of the layer containing at least one thermoplastic excipient.

The second step of the process according to the invention consists in depositing the polymer film which allows protection of the active principle, masking of the taste, or modified and controlled release of the active principle. The polymer coating preparation can be in the form of solutions or dispersions in aqueous or organic medium.

The third optional step of the process according to the invention consists in depositing the protective outer layer by spraying the coating preparation, which can be in the form of a solution or dispersion in aqueous or organic medium.

It is advantageously possible, as need be, to add an anti-adhesive agent such as talc, a plasticizer such as polyethylene glycol, and an antioxidant such as dl-α-tocopherol to the coating and assembly preparations.

It is advantageously possible to add a disintegrating agent to the protective outer layer so as to accelerate the release of the spheroids in aqueous medium, when these have been tabletted.

The disintegrating agent is, for example, crosslinked carboxymethylcellulose, crosslinked polyvinyl-pyrrolidone or sodium carboxymethyl starch.

The subject of the present invention is also multiparticulate pharmaceutical preparations containing the spheroids described above, which can be obtained by the process of the invention.

The pharmaceutical preparations of the present invention each preferably contain a unit dose of between 0.5 and 100 mg of tiagabine and are administered daily.

The multiparticulate pharmaceutical preparations according to the invention are preferably in the form of gelatin capsules filled with the said spheroids, or tablets of the said spheroids.

The said tablets are advantageously prepared without the substantial addition of auxiliary substances. Before compression, up to 5% by weight of a lubricant such as talc can be added to the spheroids.

The said tablets advantageously comprise spheroids protected by a water-dispersible layer consisting of an acrylic, vinyl or cellulose polymer or a water-dispersible thermoplastic excipient, or any other excipient which is soluble in aqueous medium.

This layer has the role of ensuring cohesion between the spheroids, of thereby ensuring the hardness of the tablet, and of allowing the tablet to disintegrate when it is immersed in solution.

The tablets according to the invention are dispersible in solution and yield independent spheroids, such that the release profile of the tablet and of the spheroids which constitute it are virtually equivalent.

The reason for this is that the tablets according to the invention allow the delivery of spheroids without adversely affecting the release profile of the tiagabine they contain under the effect of the compression.

The tablets according to the invention can be composed solely of spheroids according to the invention, or of a mixture of spheroids according to the invention and of placebo spheroids, that is to say spheroids in accordance with the present invention but lacking the active principle.

The stresses exerted on the spheroids, during the compression step, can range from 5 kN to 50 kN, preferably between 5 kN and 15 kN.

The hardness of the tablets is preferably between 10 N and 100 N, more preferably between 10 N and 50 N.

The disintegration time of the tablets in aqueous medium at 37° C. is less than 60 min.

The tablets according to the invention preferably have a mass of between 0.1 g and 1 g.

They may be round, oval or oblong in shape, they may have a flat or concave surface and may have cleaving grooves or bars.

The tablets according to the invention can be subjected to a final protective or colouring coating operation.

Lastly, the subject of the present invention is the use of a pharmaceutical preparation described above, for the manufacture of a medicinal product which is useful for treating epilepsy, the said medicinal product preferably being in the form of a tablet.

The present invention will be described more particularly with the aid of the examples which follow and of the single figure, which should not be considered as limiting the invention.

The single figure represents the percentage by mass of in-vitro dissolution of tiagabine for the non-compressed spheroids according to the invention (curve 1) and for a tablet of spheroids according to the invention (curve 2).

BRIEF DESCRIPTION OF THE DRAWING

The single FIGURE shows two curves representing percentage by mass of tiagabine over time.

EXAMPLE 1

Assembly Step

Preparation of the Assembly Suspension

Weigh out the excipients in the proportions given below.

| Materials | Amount (g) | Percentage |
|---|---|---|
| Tiagabine | 100.0 | 52.1% of the dry extract |
| Novata AB ® wax | 38.0 | 19.8% of the dry extract |
| PEG-6000 | 13.0 | 6.8% of the dry extract |
| Polysorbate 80 | 6.0 | 3.1% of the dry extract |
| dl-α-Tocopherol | 10.0 | 5.2% of the dry extract |
| Talc | 25.0 | 13.0% of the dry extract |
| Purified water | 233.0 | 100% of the solvent |

Dry extract content: 45.2%

Heat the purified water to 37° C.,

Add the PEG-6000 (Empakol®—sold by ICI) and melt it until a homogeneous solution is obtained, Heat the Novata AB® wax (sold by Henkel) to 37° C.

Add the polysorbate 80 wax (sold by ICI) and the dl-α-tocopherol (sold by Roche), Mix at 37° C., using a Heidolph-type stirrer, the aqueous solution and the oily solution in order to obtain an oil-in-water type emulsion, Cool so as to bring the temperature down to about 25° C., Add the active principle, Grind the suspension using an Ultra-Turrax® type turbomixer, Lastly, add the talc and keep the suspension stirring during the assembly operation.

Assembly on Neutral Cores

Place 550 g of Neutres 30® (sold by NP-Pharm) into a granulating turbomixer, a perforated turbomixer or a fluidized-airbed, Carry out the assembly continuously by spraying of the suspension described above, Maintain the temperature between 20 and 23° C. throughout the operation, Sieve the mass of microgranules obtained.

Final Formula

| Materials | Percentage |
|---|---|
| Neutres 30 ® | 74.1% |
| Tiagabine | 13.5% |
| Novata AB ® wax | 5.1 |
| PEG-6000 | 1.8% |
| Polysorbate 80 | 0.8% |
| dl-α-Tocopherol | 1.3% |
| Talc | 3.4% |
| Theoretical tiagabine content | 135 mg/g |

Coating Step

1. Preparation of the sustained-release coating suspension

Weigh out the following coating excipients in the proportions indicated:

| Materials | Amount (g) | Percentage |
|---|---|---|
| Eudragit NE 30D ® | 40.0 g | 80.0% of dry extract |
| PEG-6000 | 10.0 g | 20.0% of dry extract |
| Purified water | 158.0 g | 100% of solvent |

Content of the dry extract: 24.0%

Place the purified water in a container with stirring,

Dissolve the PEG-6000 until a homogeneous solution is obtained,

Add the Eudragit NE 30D® (sold by the company Röhm) slowly and stir until a homogeneous suspension is obtained, Maintain the stirring throughout the coating phase.

Coating of the Assembled Spheroids

Place a fraction of the microgranules obtained according to Example 1 into a perforated turbomixer or a fluidized-airbed, Coat the assembled spheroids by continuous spraying of the suspension described above while maintaining the bed of spheroids at a temperature below 25° C., Dry and then sieve the bulk that is obtained.

2. Preparation of the protective-coating suspension

Weigh out the following coating excipients in the proportions indicated:

| Materials | Amount (g) | Percentage |
|---|---|---|
| Opadry OYB ® | 95.0 | 95.0% of dry extract |
| PEG-6000 | 5.0 | 5.0% of dry extract |
| Purified water | 1000 | 100% of solvent |

Content of the dry extract: 10.0%

Place the purified water in a container with stirring,

Dissolve the PEG-6000 until a homogeneous solution is obtained,

Add the Opadry OYB® (sold by the company Colorcon) slowly and stir until a homogeneous suspension is obtained, Maintain the stirring throughout the coating phase.

Coating of the Sustained-Release Spheroids

Place a fraction of the spheroids obtained above into a perforated turbomixer or a fluidized-airbed, Coat the sustained-release spheroids by continuous spraying of the solution described above while maintaining the bed of spheroids at a temperature below 25° C., Dry at 30°/35° C. at the end of the coating and then sieve the bulk thus obtained.
Final Formula Corresponding to 35% w/w of Prolonged-Release Coating and 5% w/w of Protective Coating

| Materials | Percentage |
|---|---|
| Neutres 30 ® | 44.9% |
| Tiagabine | 8.2% |
| Novata AB ® wax | 3.1% |
| PEG-6000 | 8.3% |
| Polysorbate 80 ® | 0.5% |
| d1-α-Tocopherol | 0.8% |
| Talc | 2.1% |
| Opadry OYB ® | 4.1% |
| Eudragit NE 30D ® | 28.0% |
| Theoretical tiagabine content | 82 mg/g |

The spheroids are then compressed on a Pette P1200 type rotary instrumented machine. The compression forces applied are between 10 kN and 30 kN.
Characteristics of the Tablets Measured on 10 Units

| Average weight | Size l × L × h (mm) | Hardness | Friability | Disintegration |
|---|---|---|---|---|
| 291 mg | 12.5 × 7.5 × 4.4 | 21N | <0.1% | 45 min |

Results of in Vitro Dissolution
Conditions
Vane dissolution machine in accordance with USP XXIII standard, <711> machine 2,
  Medium: 900 ml of purified water at 37° C. stirred at 50 revolutions/minute.
  The active principle is assayed continuously by ultraviolet spectrophotometry.
  The table below gives the percentage of active principle released by the spheroids before and after compression as a function of time.

| Time (h) | Spheroids Percentage of tiagabine released | Dispersible tablets Percentage of tiagabine released |
|---|---|---|
| 0 | 0 | 0 |
| 1 | 20.1 | 22.8 |
| 2 | 32.6 | 37.6 |
| 3 | 43.2 | 49.5 |
| 4 | 52.4 | 59.1 |
| 5 | 60.5 | 67.0 |
| 6 | 67.4 | 73.4 |
| 8 | 78.0 | 82.7 |
| 12 | 89.8 | 92.8 |
| 16 | 95.4 | 97.6 |
| 23 | 99.1 | 100.6 |

The results presented in the single FIGURE show that there is no significant difference between the dissolution profiles of the active principle before and after compression.

EXAMPLE 2

This is carried out in the same way as in Example 1, but the phase of cooling the assembly suspension is eliminated.
The assembly is prepared while maintaining the temperature of the preparation at 37° C. with stirring.

EXAMPLE 3

This is performed in the same way as in Example 1, but leaving out the PEG-6000 from the assembly step:

| Materials | Amount (g) | Percentage |
|---|---|---|
| Tiagabine | 100.0 | 52.1% of the dry extract |
| Novata AB ® wax | 51.0 | 26.6% of the dry extract |
| Polysorbate 80 | 6.0 | 3.1% of the dry extract |
| d1-α-Tocopherol | 10.0 | 5.2% of the dry extract |
| Talc | 25.0 | 13.0% of the dry extract |
| Purified water | 233.0 | 100% of the solvent |

Dry extract content: 45.2%

What is claimed is:
1. Spheroids containing tiagabine as active principle and comprising:
  a core, or
  a core coated with a layer, said layer containing at least one thermoplastic excipient which is of pasty to semi-solid consistency at a temperature of about 20° C., and whose melting point is between about 25° C. and about 100° C.,
    said core or said layer being coated with
      a flexible and deformable film, based on a polymer material, whose glass transition temperature is less than about 30° C., which ensures either protection or masking of the taste, or modified and controlled release of the tiagabine.
2. Spheroids according to claim 1, wherein said thermoplastic excipient is selected from the group consisting of partially hydrogenated oils, beeswax, carnauba wax, paraffin waxes, silicone waxes, C12–C18 fatty alcohols C12–C18 fatty acids, solid, semi-synthetic glycerides, glycerol monoesters, glycerol diesters, glycerol triesters, polyoxyethylene glycols, glycosylated polyoxyethylenated glycerides, and mixtures thereof.
3. Spheroids according to claim 1, wherein said glass transition temperature of the flexible and deformable film is less than about 20° C.
4. Spheroids according to claim 1, wherein said polymer material is a polymer or a mixture of at least one polymer and a plasticizer.
5. Spheroids according to claim 4, wherein said plasticizer is selected from the group consisting of triethyl citrate, acetyl triethyl citrate, tributyl citrate, acetyl tributyl citrate, triacetin, diethyl phthalate, polyethylene glycols, polysorbates, mono-glycerides, diacetylated glycerides, and mixtures thereof.
6. Spheroids according to claim 1, wherein said polymer material has a percentage of elongation of greater than about 50%.
7. Spheroids according to claim 1, wherein said spheroids are coated with a water-dispersible outer layer which provides said spheroids with cohesion during an optional compression step and which ensures breakdown in aqueous medium of the tablet obtained.
8. Spheroids according to claim 7, wherein said water-dispersible outer layer consists of an acrylic, vinyl or cellulose polymer.
9. Spheroids according to claim 1, wherein said tiagabine is dispersed in the bulk of the core.
10. Spheroids according to claim 1, wherein said tiagabine is dispersed in the layer containing at least one thermoplastic excipient.
11. Spheroids according to claim 1, wherein said tiagabine is applied to the surface of the core and then coated with a layer containing at least one thermoplastic excipient.
12. Spheroids according to claim 1, wherein said tiagabine is dispersed in the bulk of the core and in the layer containing at least one thermoplastic excipient.

13. The spheroids according to claim 7, wherein 5% by weight of a lubricant is added to the spheroids before said compression step.

14. Multiparticulate pharmaceutical preparations containing the spheroids according to claim 1.

15. Pharmaceutical preparations according to claim 14, wherein each preparation contains a unit dose of between 0.5 and 100 mg of tiagabine.

16. Pharmaceutical preparations according to claim 14, wherein said pharmaceutical preparations are in the form of gelatin capsules filled with said spheroids.

17. Pharmaceutical preparations according to claim 14, wherein said pharmaceutical preparations are in the form of tablets of said spheroids.

18. The pharmaceutical preparations according to claim 14, wherein said preparations do not contain a substantial amount of auxiliary substance.

19. A method of treating epilepsy comprising administering to an epileptic an epilepsy treating amount of the spheroids of claim 1.

* * * * *